US011852629B2

(12) United States Patent
Loos et al.

(10) Patent No.: US 11,852,629 B2
(45) Date of Patent: Dec. 26, 2023

(54) METHOD AND DEVICE FOR DETERMINING AUTOPHAGIC FLUX

(71) Applicant: Stellenbosch University, Stellenbosch (ZA)

(72) Inventors: Benjamin Loos, Stellenbosch (ZA); Jan Hendrik Servaas Hofmeyr, Stellenbosch (ZA); Willem Jacobus Perold, Stellenbosch (ZA); Andre Du Toit, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 307 days.

(21) Appl. No.: 17/254,489

(22) PCT Filed: Jul. 1, 2019

(86) PCT No.: PCT/IB2019/055604
§ 371 (c)(1),
(2) Date: Dec. 21, 2020

(87) PCT Pub. No.: WO2020/003286
PCT Pub. Date: Jan. 2, 2020

(65) Prior Publication Data
US 2021/0116446 A1    Apr. 22, 2021

(30) Foreign Application Priority Data

Jun. 29, 2018    (ZA) .................................. 2018/04374

(51) Int. Cl.
*G01N 33/543*      (2006.01)
*G01N 33/68*       (2006.01)

(52) U.S. Cl.
CPC ..... *G01N 33/5438* (2013.01); *G01N 33/6845* (2013.01)

(58) Field of Classification Search
None
See application file for complete search history.

(56) References Cited

U.S. PATENT DOCUMENTS 7,208,077 B1    4/2007    Albers et al.

FOREIGN PATENT DOCUMENTS

| WO | 2007067759 A2 | 6/2007 |
| WO | 2017195130 A1 | 11/2017 |

OTHER PUBLICATIONS

Karim, et al., "Cytosolic LC3 Ratio as A Sensitive Index of Macroautophagy in Isolated Rat Hepatocytes and H4-II-E Cells", Autophagy, 3(6): p. 553-560, Nov (Year: 2007).*

(Continued)

*Primary Examiner* — J. Christopher Ball
(74) *Attorney, Agent, or Firm* — Dinsmore & Shohl LLP; Weston R. Gould

(57) ABSTRACT

A method, device and system for determining autophagic flux are claimed. The levels of proteins which change with increased or decreased autophagy are determined in a sample. The change in the level of each protein is quantified in order to obtain the autophagic flux. This can be compared to a sample flux range associated with autophagy dysfunction or ageing patterns. Diseases or conditions which may be diagnosed include neurodegenerative conditions such as Alzheimer's disease and dementia, cancer, heart conditions, immune conditions or aging-related conditions. The device for determining autophagic flux comprises a housing, receiving zones configured for receiving a substrate and a biological sample, and a set of electrodes for each receiving zone. The device is connectable to circuitry that determines an electrical property of each substrate and uses this to determine the autophagic flux.

12 Claims, 13 Drawing Sheets

(56) References Cited

OTHER PUBLICATIONS

S. McGraw, et al., "A Resistance Based Biosensor That Utilizes Conductive Microbial Pathogen Detection", Open Journal of Applied Biosensor, 1, p. 36-43 (Year: 2012).*
International Search Report and Written Opinion pertaining to PCT/IB2019/055604, dated Aug. 22, 2019.
Loos et al., "Defining and Measuring Autophagosome Flux Concept and Reality", Autophagy, 2014, 2087-2096.
Leisching et al.,"The Role of mTOR During Cisplatin Treatment in Anin Vitroandex Vivomodel of Cervical Cancer", Toxicology, 2015, 72-78.
Zhu et al., "FGF21 Ameliorates Nonalcoholic Fatty Liver Disease by Inducing Autophagy", Molecular and Cellular Biochemistry, 2016, 107-119.

* cited by examiner

Key

Proteins involved in autophagy:
1. Cytoplasmic dynein 1 heavy chain 1, 2. Cytoplasmic dynein 1 light intermediate chain 1, 3. Dynein light chain 2 cytoplasmic, 4. Dynein light chain 1 cytoplasmic, 5. Cytoplasmic dynein 1 light intermediate chain 2, 6. General vesicular transport factor p115, 7. Tubulin beta-2A chain, 8. Tubulin beta-4B chain, 9. Microtubule-associated protein 1S, 10. Microtubule-actin cross-linking factor 1, 11. Lysosome-associated membrane glycoprotein 2, 12. Lysosome-associated membrane glycoprotein 1, 13. Cysteine protease ATG4B, 14. Microtubule-associated proteins 1A/1B light chain 3B No change:
15. Serpin H1, 16. Peroxiredoxin 6, 17. 6-phosphogluconolactonase, 18. Twinfilin-1, 19. DnaJ homolog subfamily B member 4, 20. Histone-binding protein RBBP4

↑ with √
21. Histone-binding protein RBBP7, 22. Protein phosphatase 1 regulatory subunit 12A, 23. Eukaryotic translation initiation factor 4H, 24. UV excision repair protein RAD23 homolog B ↓ with √
25. T-complex protein 1 subunit eta, 26. Glyceraldehyde-3-phosphate dehydrogenase, 27. Alanine–tRNA ligase cytoplasmic, 28. L-lactate dehydrogenase A chain, 29. Serine hydroxymethyltransferase, 30. Stress-70 protein mitochondrial, 31. V-type proton ATPase catalytic subunit A, 32. Coatomer subunit alpha, 33. Coatomer subunit gamma-1, 34. Delta-1-pyrroline-5-carboxylate synthase, 35. Glycine–tRNA ligase, 36. Protein transport protein Sec31A, 37. Ubiquitin carboxyl-terminal hydrolase 5, 38. Asparagine synthetase [glutamine-hydrolyzing], 39. Phosphoenolpyruvate carboxykinase [GTP] mitochondrial, 40. Serine–tRNA ligase cytoplasmic, 41. Aspartate aminotransferase mitochondrial, 42. Acetoacetyl-CoA synthetase, 43. 4F2 cell-surface antigen heavy chain, 44. Dynamin-2, 45. Cysteine–tRNA ligase cytoplasmic, 46. Protein Qars, 47. Protein RCC2, 48. Proteasome subunit alpha type-6, 49. Sorting nexin 3, 50. Leukotriene A-4 hydrolase, 51. Sequestosome-1, 52. UDP-N-acetylhexosamine pyrophosphorylase-like protein 1, 53. Protein Gm43738, 54. Isopentenyl-diphosphate Delta-isomerase 1, 55. 40S ribosomal protein S12, 56. Sorting nexin-2, 57. Developmentally-regulated GTP-binding protein 1, 58. Malectin, 59. Signal transducer and activator of transcription 1, 60. Phosphoserine phosphatase, 61. Serine/threonine-protein kinase DCLK1, 62. N-terminal kinase-like protein, 63. E3 ubiquitin-protein ligase TRIM32, 64. Beta-1,4-galactosyltransferase 5

FIG. 13, cont.

METHOD AND DEVICE FOR DETERMINING AUTOPHAGIC FLUX

CROSS-REFERENCE TO RELATED APPLICATIONS

This application is a National Stage Entry under 35 U.S.C. § 371 of International Patent Application No. PCT/IB2019/055604 filed on 1 Jul. 2019, which claims priority from South African provisional patent application number 2018/04374 filed on 29 Jun. 2018.

FIELD OF THE INVENTION

The invention provides a method and device for determining autophagic flux, and hence for diagnosing autophagy dysfunction in a subject and diseases or conditions associated with autophagy.

BACKGROUND OF THE INVENTION

Autophagy is a degradative pathway that is active in all eukaryotic systems in order to clear long-lived proteins. Many pathologies are associated with a change in autophagic activity, such as neurodegeneration (diminished autophagy), cancer (enhanced autophagy), heart disease and immunity. Macroautophagy is crucial for preventing neuronal protein aggregation and the onset of neurodegenerative disease. Dysfunction in autophagy has been indicated in Alzheimer's disease (AD), Parkinson's disease and Huntington's disease. Autophagy also progressively declines in ageing.

Most autophagy research is centred around neurodegenerative diseases (in particular Alzheimer's disease), for which diagnosis and treatment are a major challenge and no disease modifying intervention is available. This is in part due to the inability to measure and subsequently control autophagy accurately with autophagy-enhancing drugs.

Although there are more than 200 research and academic institutions engaged in autophagic research, the measurement of autophagy remains a challenge. This is due to the dynamic character of autophagy which, similarly to a blood-clotting test, has to be measured over time. Leading recommendations for measuring and interpreting autophagic flux are static in nature, providing no direct read-out for autophagic activity, and there is currently no available device that measures the rate of autophagy.

The inability to accurately measure the rate of autophagy is a problem in both the drug development and clinical arenas. For example, pharmaceutical institutions do not know how to interpret their autophagy drug-screening results precisely and so identify autophagy modulating compounds, and clinicians are unable to ascertain the autophagy status of patients/tissues.

SUMMARY OF THE INVENTION

According to a first aspect of the invention, there is provided a method for determining autophagic flux, the method comprising the steps of:
    determining the level of at least two proteins in a biological sample from a subject, wherein the proteins are proteins which are overexpressed or underexpressed with a change in autophagic flux; and
    comparing the level of each protein to the level of each of the other proteins and obtaining a flux value for the sample.

The flux value of the sample may be compared to a predetermined flux value or range associated with a known autophagy flux in order to determine whether there is autophagy dysfunction in the subject.

The autophagy dysfunction may be an indicator of a neurodegenerative disease or condition such as Alzheimer's disease or dementia, or may be cancer, a heart condition, an immune condition or an aging-related condition.

The level of each protein may also be compared to the level of a reference protein for an inherent loading control. The reference protein for the loading control may be a protein which is not differently expressed with a change in autophagy, such as DnaJ homolog subfamily B member 4 or Beta-actin.

The proteins may be captured onto a substrate and the amount of captured protein may be determined when determining the level of the protein in the sample.

The proteins may be selected from Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin, Phospho-mammalian target of rapamycin and the like.

The method may comprise determining the levels of 3 proteins in the sample, 4 proteins in the sample, 5 proteins in the sample, 6 proteins in the sample, 7 proteins in the sample, 8 proteins in the sample, 9 proteins in the sample, 10 proteins in the sample, 11 proteins in the sample, 12 proteins in the sample, 13 proteins in the sample, 14 proteins in the sample, 15 proteins in the sample, 16 proteins in the sample, 17 proteins in the sample, 18 proteins in the sample, 19 proteins in the sample, 20 proteins in the sample, and so forth.

Capture agents may be used to capture the proteins onto the substrate. The capture agents may be antibodies or antibody fragments, affybodies, ankyrin repeat proteins, armadillo repeat proteins, nucleic acid aptamers, peptides, carbohydrate ligands, synthetic ligands, luminescent conjugated oligothiophene (LCO) markers or synthetic polymers. More preferably, the capture agents are antibodies.

The substrate may be made from carbon, and may be in the form of a nanofibre or a nanowire. The nanofibre or nanowire may be electrically conductive or contain an electrically conductive coating or weave.

The capture agent may be bound to the substrate.

The amount of protein captured on the substrate may be determined by measuring the electrical resistance across the substrate. Binding of the protein to the capture agent may cause electrical resistance across the substrate to change, the resistance corresponding to a level of the protein in the sample.

Alternatively, acoustic, optical or mechanical means may be used to determine how much protein is captured to the substrate.

The biological sample may be from whole blood, blood plasma, blood serum, urine, saliva, sputum, or tissue obtained from a biopsy. More particularly, the biological sample may be a protein lysate generated from a tissue biopsy, cells or peripheral blood.

The method may also include the step of measuring the voltage across the substrate, as this will also change with binding of the protein.

The resistance and voltage signals may be amplified, converted to digital signals and/or recorded.

According to a second aspect of the invention, there is provided a method for diagnosing autophagy dysfunction in a subject, the method comprising the steps of:
performing the method described above; and
diagnosing autophagy dysfunction in the subject if the relative protein levels of at least one of the proteins in the sample is higher or lower than a reference value for that protein.

The autophagy dysfunction may be a neurodegenerative disease or condition such as Alzheimer's disease or dementia, or may be cancer, a heart condition, an immune condition or an aging-related condition.

According to a third aspect of the invention, there is provided a method for treating a subject, the method comprising the steps of:
performing the method described above;
diagnosing a disease or condition in the subject by comparing the relative changes in the levels of the proteins to a reference value or range associated with a known autophagy; and
administering an effective amount of an autophagy-modulating drug to the subject if the subject is in need thereof.

The autophagy-modulating drug may be an autophagy enhancing drug or may be an autophagy inhibiting drug.

According to a fourth aspect of the invention, there is provided a device for determining autophagic flux in a sample from a subject, the device comprising:
a housing;
a plurality of receiving zones located in the housing, each receiving zone configured for receiving a substrate and a portion of a biological sample from a subject;
a set of electrodes for each receiving zone, each set of electrodes positioned in the housing so as to extend into a receiving zone and, when the substrate is in the receiving zone, to come into contact with the substrate;
wherein each set of electrodes is connectable to circuitry that is arranged to determine an electrical property of each substrate and to use the determined electrical property of each substrate to determine the autophagic flux in the biological sample.

The substrate may be optionally included as part of the device. The substrate may be a carbon substrate, and may be in the form of nanofibres or nanowires. The substrate may be removeable.

The substrate may be coated with the capture agents for binding proteins from the sample or may be configured to be coated with capture agents. The capture agents may be as described above.

The housing may include separable upper and lower parts. The receiving zones may be located in the lower part of the housing. The upper part of the housing may be configured to attach onto the lower part so that each receiving zone is covered and so that the electrodes come into contact with the substrate when the substrate is in the receiving zones.

At least a subset of the circuitry may be provided on a separate circuit board connectable to the electrodes via conductors such as a multicore cable.

The electrical characteristic may be a resistance of the substrate and the circuitry may include a resistance determining component in communication with the electrodes arranged to determine a resistance of the relevant substrate; a resistance comparing component for comparing each resistance measurement to the other resistance measurements and assigning a flux value to the sample; and an output component configured to output a result.

The result of the output may indicate the autophagic flux of the sample or whether or not the subject has autophagy dysfunction.

The circuitry may further determine how much of each protein is captured onto the substrate.

The device may be a point-of-care device.

According to a fifth embodiment of the invention, there is provided a kit comprising:
capture agents for binding at least two proteins selected from Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin, Phospho-mammalian target of rapamycin, or any other proteins which are over-expressed or under-expressed when there is a change in autophagic flux;
a device as described above;
two or more substrates as described above (with or without capture agents);
a buffer for preparing a protein lysate sample from a biological sample; and/or instructions in printed or electronic form for performing the method described above.

The capture agents may be as described above.

According to a sixth embodiment of the invention, there is provided a system for detecting a level of autophagic flux in a subject according to the method described above, the system including:
a plurality of substrates, each for contacting a biological sample and binding a protein of interest in the sample;
a sensor for measuring the resistance and optionally also the voltage across each substrate;
a processor; and
an output member in communication with the processing means configured to output a result indicating a level of autophagic flux in the subject based on the relative resistance measurements for each substrate.

The system may further include software components and/or a storage means.

According to a seventh embodiment of the invention, there is provided a computer implemented method for diagnosing autophagy dysfunction in a subject, the computer performing steps comprising:
receiving inputted subject data comprising values corresponding to levels of two or more proteins in a biological sample from the subject;
comparing the level of each protein to the levels of the other proteins;
assigning a flux value for the sample; and
displaying information regarding whether the subject has autophagy dysfunction or not.

The inputted subject data may comprise resistance readings corresponding to the amount of the proteins in the biological sample.

The computer-implemented method may further comprise recording, analysing and/or processing the inputted subject data; determining an amount of each protein in the sample;

determining the relative amounts of each protein in the sample; and assigning a level of flux based on the relative amounts of protein detected.

DETAILED DESCRIPTION OF THE INVENTION

The invention provides a method, device and system for determining autophagic flux, wherein the level of at least two proteins which change with increased or decreased autophagy are determined in a biological sample from a subject. The change in the level of each protein relative to the changes in the levels of the other protein(s) is quantified in order to obtain an indication of the level of autophagic flux in the sample. This can then be compared to a predetermined sample flux range associated with known autophagy dysfunction or associated with known ageing patterns (including exercise and caloric restriction), and this comparison can be used to make a diagnosis of autophagy dysfunction (or a disease or condition which is related to autophagy dysfunction) or successful ageing in the subject. The disease or condition may be a neurodegenerative disease or condition such as Alzheimer's disease or dementia, or may be cancer, a heart condition, an immune condition or an aging-related condition. The method could also be used in the health and wellness sectors associated with lifestyle to predict successful ageing.

As used herein, the term "autophagy dysfunction" refers to a condition where the autophagic flux in a subject is reduced or increased relative to the autophagic flux in a healthy subject.

Throughout the specification, unless the contents require otherwise, the word 'comprise' or variations such as 'comprises' or 'comprising' will be understood to imply the inclusion of a stated integer or group of integers but not the exclusion of any other integer or group of integers.

Autophagy-modulating drugs can be administered to a subject who is diagnosed with autophagy dysfunction or an autophagy-related disease or condition. Depending on whether autophagy in the subject is up-regulated or down-regulated, the autophagy-modulating drug can be an autophagy enhancing drug (e.g. rapamycin and spermidine) or may be an autophagy inhibiting drug (e.g. 3 methyl adenine or chloroquine).

Figure 1:
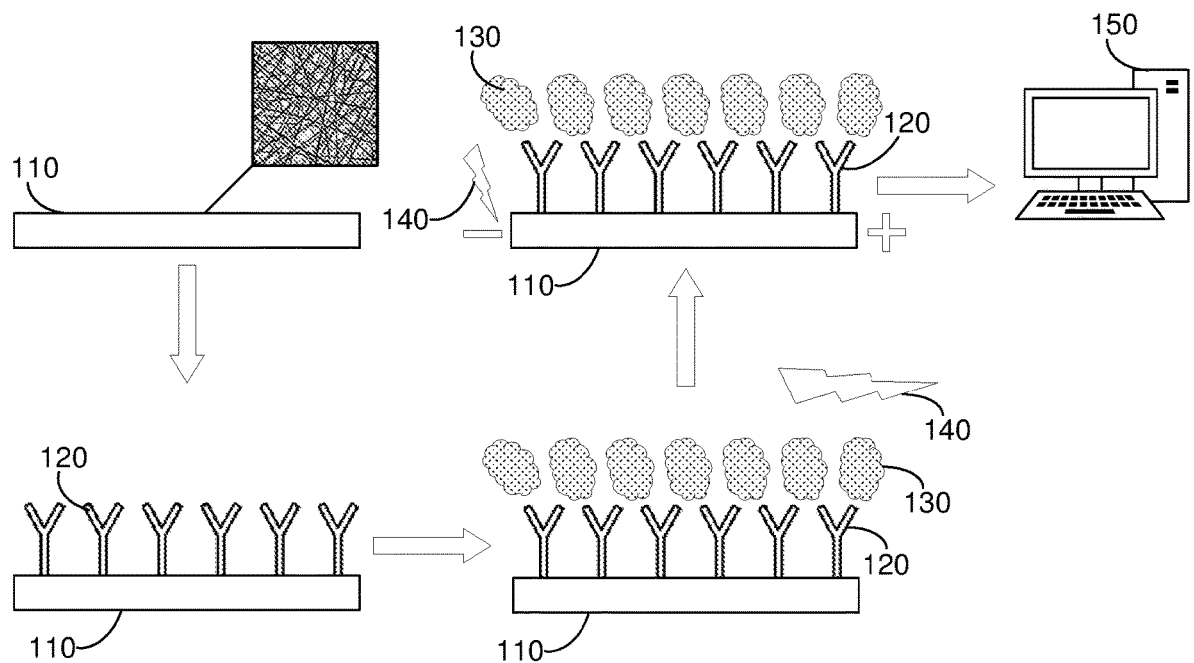
FIG. 1 is a schematic representation of an embodiment of the method of the invention in which a capture agent (an antibody) for a protein is secured to a substrate. The resistance of the substrate and resistance changes upon binding of the protein to the substrate are measured. A computing device is programmed to record and compare resistance readings and to provide an indication of autophagic flux in a sample.
Figure 5:
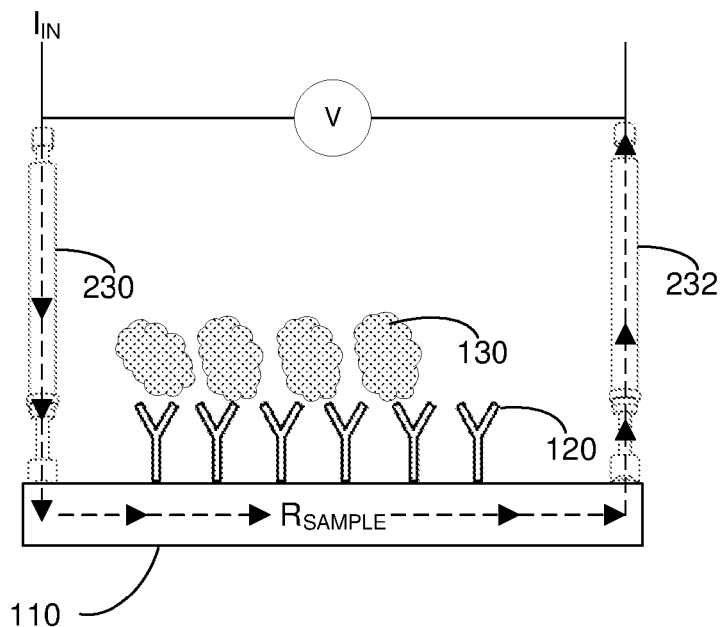
FIG. 5 is a schematic representation of an embodiment of a system according to the invention in which a sample is analysed by a resistance detector in communication with a constant current source.
Figure 9:
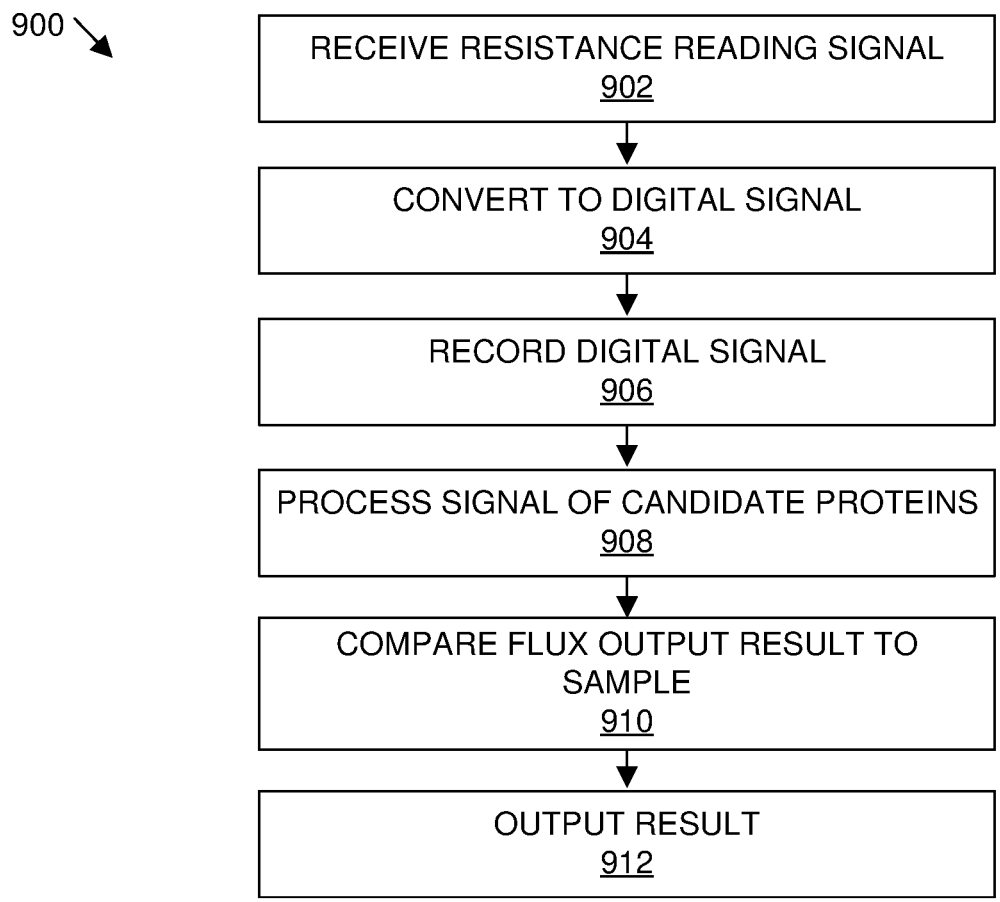
FIG. 9 is a flow diagram illustrating steps of a computer-implemented method according to the invention.

One embodiment of the method is schematically represented in FIGS. 1, 5 and 9. A portion of a biological sample from a subject is brought into contact with a first substrate (110) having capture agents (120) which are biorecognition agents which specifically bind a first protein (130) of interest. If this first protein is present in the sample, at least some of it will become bound to the substrate via the capture agents. The amount of protein captured on the substrate can be determined, which corresponds to the total amount of that protein in the sample. An equal portion of the same biological sample is brought into contact with a second substrate of the same type as the first substrate, except that the second substrate has capture agents which bind a second protein of interest. In the same manner as described above, the amount of the second protein captured on the second substrate can be determined. This process can be repeated for any number of additional proteins, although in order to lower the costs of performing the method, the method is generally limited to 20 proteins or fewer, such as no more than 18 proteins, no more than 16 proteins, no more than 14 proteins, no more than 12 proteins, no more than 10 proteins, no more than 8 proteins, no more than 6 proteins, no more than 4 proteins, and so forth.

The biological sample can be whole blood, blood plasma, blood serum, cells or tissue obtained from a biopsy. When the biological sample is tissue from a biopsy (e.g. brain tissue, cancer tissue), the sample will provide tissue-specific autophagic flux. On the other hand, a blood sample (e.g. from peripheral blood) will provide a value for patient-specific systemic autophagic flux. A protein lysate can be prepared from the sample for use in the method, and a buffer such as RIPA can be added to the protein lysate.

The proteins which are of interest are proteins which are overexpressed or underexpressed in a subject when the autophagic flux changes, examples of which include Cytoplasmic dynein 1 heavy chain 1, Cytoplasmic dynein 1 light intermediate chain 1, Dynein light chain 2 cytoplasmic, Dynein light chain 1 cytoplasmic, Cytoplasmic dynein 1 light intermediate chain 2, General vesicular transport factor p115, Tubulin beta-2A chain, Tubulin beta-4B chain, Microtubule-associated protein 1S, Microtubule-actin cross-linking factor 1, Lysosome-associated membrane glycoprotein 2, Lysosome-associated membrane glycoprotein 1, Cysteine protease ATG4B, Microtubule-associated proteins 1A/1B light chain 3B, Serpin H1, Peroxiredoxin 6, Twinfilin-1, DnaJ homolog subfamily B member 4, Histone-binding protein RBBP4, Histone-binding protein RBBP7, Protein phosphatase 1 regulatory subunit 12A, Eukaryotic translation initiation factor 4H, UV excision repair protein RAD23 homolog B, T-complex protein 1 subunit eta, Glyceraldehyde-3-phosphate dehydrogenase, Alanine-tRNA ligase cytoplasmic, L-lactate dehydrogenase A chain, Serine hydroxymethyltransferase, Stress-70 protein mitochondrial, V-type proton ATPase catalytic subunit A, Coatomer subunit alpha, Coatomer subunit gamma-1, Delta-1-pyrroline-5-carboxylate synthase, Glycine-tRNA ligase, Protein transport protein Sec31A, Ubiquitin carboxyl-terminal hydrolase 5, Asparagine synthetase [glutamine-hydrolyzing], Phosphoenolpyruvate carboxykinase [GTP] mitochondrial, Serine-tRNA ligase cytoplasmic, Aspartate aminotransferase mitochondrial, Acetoacetyl-CoA synthetase, 4F2 cell-surface antigen heavy chain, Dynamin-2, Cysteine-tRNA ligase cytoplasmic, Protein Qars, Protein RCC2, Proteasome subunit alpha type-6, Sorting nexin 3, Leukotriene A-4 hydrolase, Sequestosome-1, UDP-N-acetylhexosamine pyrophosphorylase-like protein 1, Protein Gm43738, Isopentenyl-diphosphate Delta-isomerase 1, 40S ribosomal protein S12, Sorting nexin-2, Developmentally-regulated GTP-binding protein 1, Malectin, Signal transducer and activator of transcription 1, Phosphoserine phosphatase, Serine/threonine-protein kinase DCLK1, N-terminal kinase-like protein, E3 ubiquitin-protein ligase TRIM32 and Beta-14-galactosyltransferase 5. More particularly, the proteins may be selected from Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin, Phospho-mammalian target of rapamycin, and others.

The method can also include measuring an electrical property, such as the resistance (and hence relative abundance) of a control protein which is independent of autophagic flux. Examples of such a protein are beta-actin or DnaJ homolog subfamily B member 4. Measuring of resistance may be direct or indirect measurement, i.e. that the resistance may be derived or calculated from another measurement and known quantities. For example, a voltage across the sample of the control protein and an electrical current flowing through sample may be measured (or at least one of these quantities known) and the resistance calculated therefrom using Ohm's law. References to measuring an increase in resistance will be understood to be equivalent to measuring a reduction in conductance and vice versa. Also, while the exemplary embodiments described herein may utilise resistance as the electrical property, it is envisaged that other electrical properties such as capacitance or inductance may be utilised. Furthermore, in the exemplary embodiments below, direct current is used. However, it is envisaged that in embodiments of the methods and systems, alternating current may be utilised, in which case references to resistance should be interpreted as impedance, and the electrical characteristics may include both the resistive and reactive components of the impedance.

Figure 8:
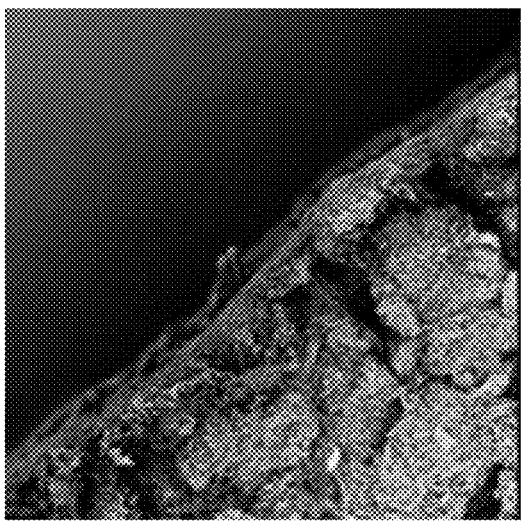
FIG. 8 shows scanning electron microscope (SEM) images of a nanowire-based carbon-coated sensing surface for use in the device of the invention.
Figure 8:
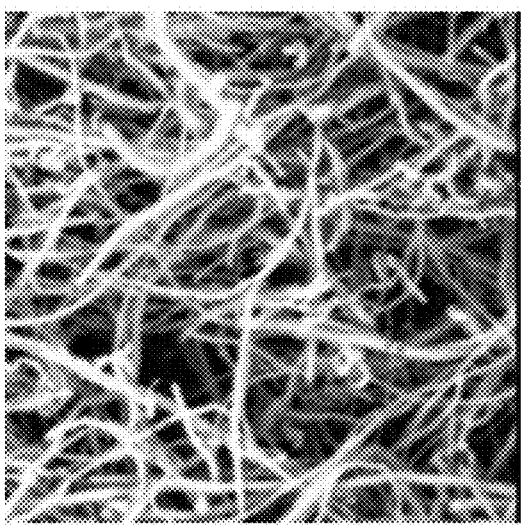
Figure 8:
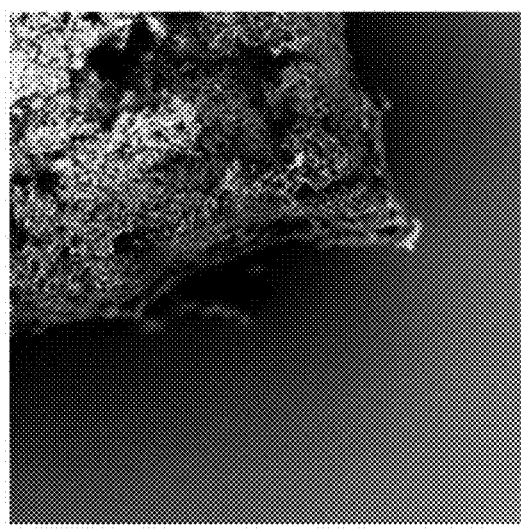

The substrate can be made from nanofibres or nanowires, and is preferably made from carbon nanofibers or nanowires (FIG. 8). These are available commercially (e.g. from Applied Sciences, Inc, P.O. Box 579, Cedarville, Ohio 45314) or can be manufactured by methods known in the art (e.g. by precision-cutting nanowires). In order to increase the surface area and durability of the substrate, multiple nanofibres or nanowires can be aggregated to form a mesh or textile, which can be a woven or a non-woven mesh or textile. The nanofibre or nanowire can be electrically conductive or contain an electrically conductive coating or electrically conductive weave.

The capture agents can be antibodies or antibody fragments, affybodies, ankyrin repeat proteins, armadillo repeat proteins, nucleic acid aptamers, peptides, carbohydrate ligands, synthetic ligands or synthetic polymers. More particularly, the capture agents are antibodies which are specific to the protein of interest.

The capture agents can be immobilized on the nanofibres or nanowires by means known in the art, e.g. by linking agents.

The amount of protein captured on the substrate can be determined by, for example, measuring the resistance of the substrate when the constant current source (140) operatively injects current into the substrate to flow therethrough. The resistance of the substrate will change (either increase or decrease) when the protein binds to it, and this change, indicating the magnitude of protein binding, can be measured over a period of time (e.g. anywhere from 10 to 30 minutes, such as 20 minutes). As the level of the protein in the sample will change with increased or decreased autophagy, the resistance reading therefore reports on and reflects this change in autophagic activity. The change in resistance values for each protein can be compared to the change in resistance values of the other proteins in order to ascertain the relative abundance of the proteins of interest. Previously obtained resistance readings of known flux samples can be used as standards, and the flux of an unknown sample can thus be derived based on the difference in resistance.

The voltage will also change as the concentration of the bound protein increases, and this can also be measured to determine the concentration of bound protein. It will be readily apparent that the measured voltage and the known value of the current produced by the constant current source (140) may be used to calculate the resistance through Ohm's law.

The resistance and voltage signals can be amplified, converted to digital signals and/or recorded. These signals can also be processed and analysed (150) in order to obtain a value of the autophagic flux in the sample.

Typically, the levels of at least 4 proteins, at least 6 proteins, at least 8 proteins, at least 10 proteins, at least 12 proteins, at least 14 proteins, at least 16 proteins, at least 18 proteins or at least 20 proteins are measured in each sample. The change in the level of each protein is compared to the change in the levels of the other proteins, relative to a non-changing protein (i.e. of a protein that does not increase or decrease with flux). Alternatively, the relative abundance of the proteins that increase with flux can be compared with the relative abundance of proteins that decrease with flux (once again, this can be relative to a non-changing protein). Thus, a signature of a combination of autophagic flux-specific proteins can be obtained from each sample and compared to a reference signature of those same proteins. The reference signature can correspond to a signature which has been found to be present in known flux samples from healthy subjects or subjects who are regarded as aging well (or even from healthy tissue from the same subject). Alternatively, the reference signature can correspond to a signature which has been found to be present in unhealthy or diseased subjects (e.g. which is higher or lower than the level of that protein generally found in healthy subjects) or subjects who are regarded as ageing early.

Figure 2:
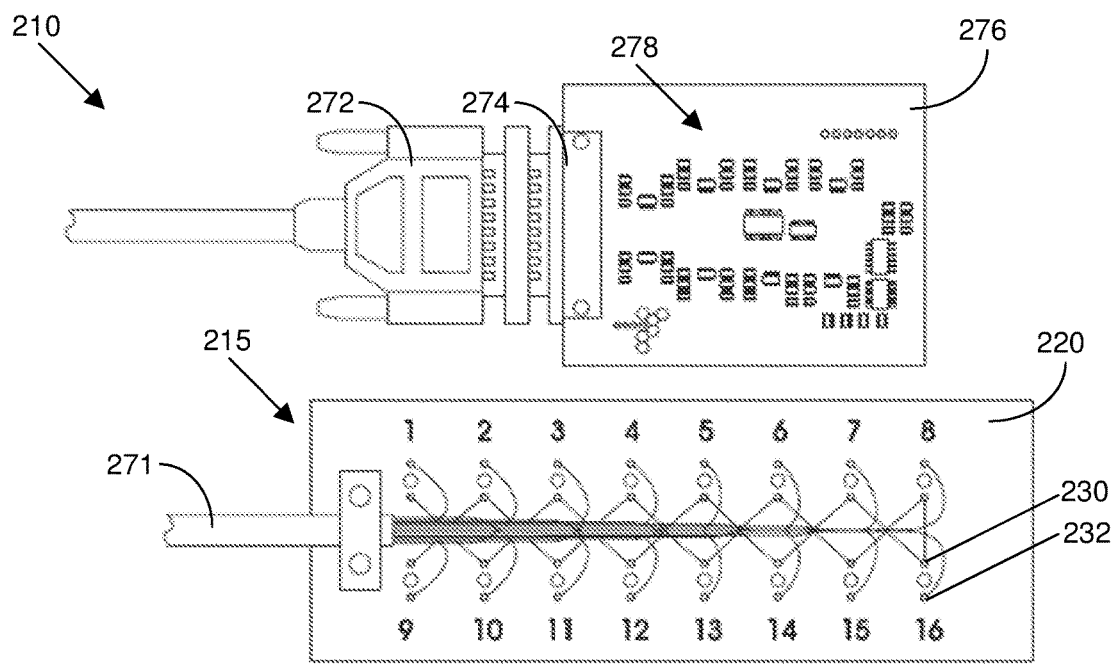
FIG. 2 shows a top view of an embodiment of a device according to the invention, for simultaneously detecting levels of up to 16 autophagic flux response proteins in a biological sample, the device being connected to a circuit board.
Figure 3:
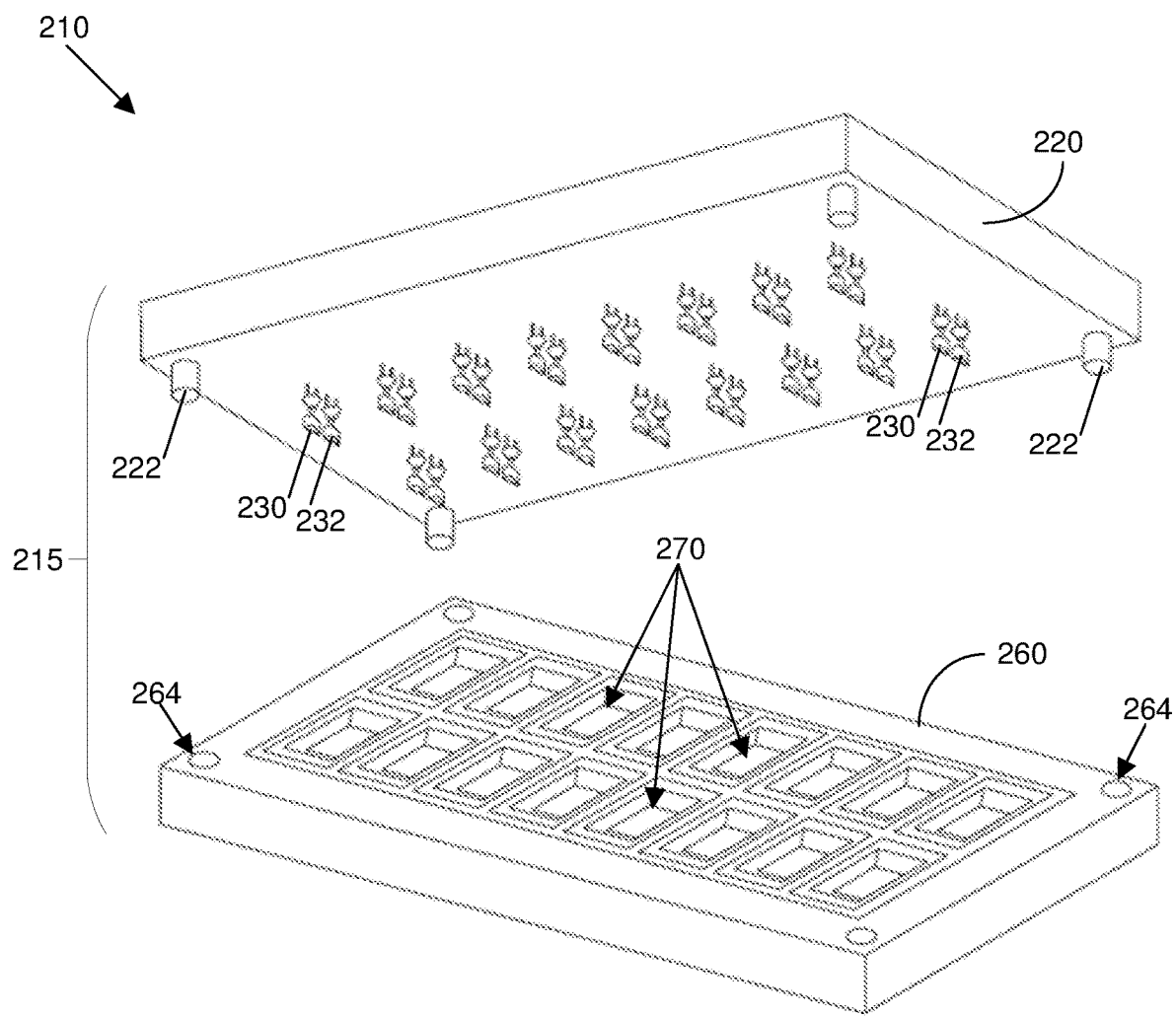
FIG. 3 shows a perspective view of the interior of a bottom part of the device of FIG. 2.

FIGS. 2 and 3 show an autophagic flux measuring device (210) for determining a level of autophagic flux in a subject in accordance with a further aspect of the invention. Components and features described with reference to the schematic view shown in FIG. 1 are referred to below in describing the functionality of the device (210). FIG. 2 shows a top view of the device (210) and FIG. 3 shows a three-dimensional side view of the device in an open configuration. The device includes a housing (215) with an upper part (220) and a lower part (260). The lower part has a plurality of receiving zones (270) sunken into it, two rows of eight receiving zones in the present embodiment. Each receiving zone (270) is configured and shaped to receive a portion of a biological sample from a subject. A substrate (110) can be placed into each receiving zone (270) in such a manner that the sample and substrate will be in contact with one another when they are in the receiving zone. Capture agents (120) for specifically binding proteins (130) can be secured to the substrate (110), the capture agents for the substrate in each receiving zone being specific to a different protein to the capture agents on the substrates in the other receiving zones.

The upper part (220) further includes four locating pins (222) extending therefrom located at each corner. The lower part (260) has corresponding locating apertures (264) configured to receive the locating pins (262) when the device is in a closed configuration, i.e. with the upper part attached atop the lower part. In the closed configuration, the upper part (220) of the device covers each receiving zone. Electrode pairs (230, 232) extend through the upper part (220) from above an upper surface (seen more clearly in FIG. 2) to below a lower surface (seen more clearly in FIG. 3). The electrodes are positioned such that when the upper part (220) is attached to the lower part (260) (i.e. when the device (210) is in a closed configuration), a pair of electrodes (230, 232) will extend into each receiving zone and make contact with the substrate in that receiving zone.

Figure 4:
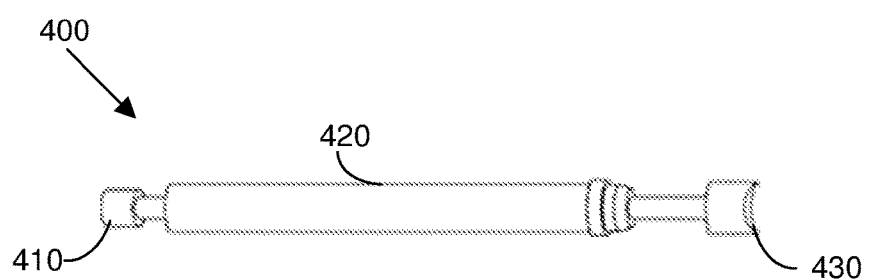
FIG. 4 shows a side view of an electrode which is utilized in the embodiment of FIG. 2, to allow a stable sample/nanowire contact interface.

FIG. 4 shows one embodiment of a suitable electrode (400). Each electrode (400) has an elongate body (420). One end of the electrode is a terminal (410) configured to be connected to conductors to and from electronic components of the device through which, for example, an electric current may be injected or a voltage measured. The other, opposite, end provides a concave contact (430). The concave configuration of the contact (430) may minimise electrode/substrate interactions upon introduction of the sample into the receiving zone and provide an even distribution of pressure at points of contact with the substrate, allowing for a stable transducer-electrode interaction. At least the concave-shaped end (430) of each electrode is gold-plated so as to minimise oxidation that might occur between the electrode and the sample. The electrode contact (430) may be removable from the body (420). This may allow the body (420) to remain installed in the upper part (220) of the device (210) while enabling the replacement of a contact if broken or worn. The electrode (400) may be spring loaded. For example, the body (420) may contain a compression spring such that when the contact (430) presses against a substrate and sample, it will be urged axially inward against the bias of the spring. This may assist in providing solid electrical connection with the substrate in use.

The terminal (410) of each electrode is electrically connected to a conductor of a multicore cable (271). The other end of the cable (271) terminates in a multiway connector, presently a male D-subminiature (DB25) connector (272), the pins of which provide electrical connection to the electrodes via the cable. The DB25 connector (272) of the cable may connect to a corresponding female DB25 connector (274) of a printed circuit board (PCB) (276). The PCB (276) houses the electronic components and circuitry (278) that facilitate the measurement of the resistance (or change in resistance) of a substrate and sample.

FIG. 5 is a simplified schematic representation of an embodiment of a system according to the invention in which a sample is analysed by the device (210). The device (210) injects an electric current ($I_{IN}$), presently with a constant current source into the substrate (110) via an electrode (230), with the return current returning to the device (210) via the other electrode (232) of the electrode pair. Since the electric current (IN) originates from a constant current source, a change in the resistance ($R_{SAMPLE}$) of the substrate (110) will cause a voltage (V) across the substrate (and thus across the electrodes) to change proportionately. This voltage may be measured with circuitry of the device (210) to derive the resistance ($R_{SAMPLE}$) of the substrate (110).

Figure 6:
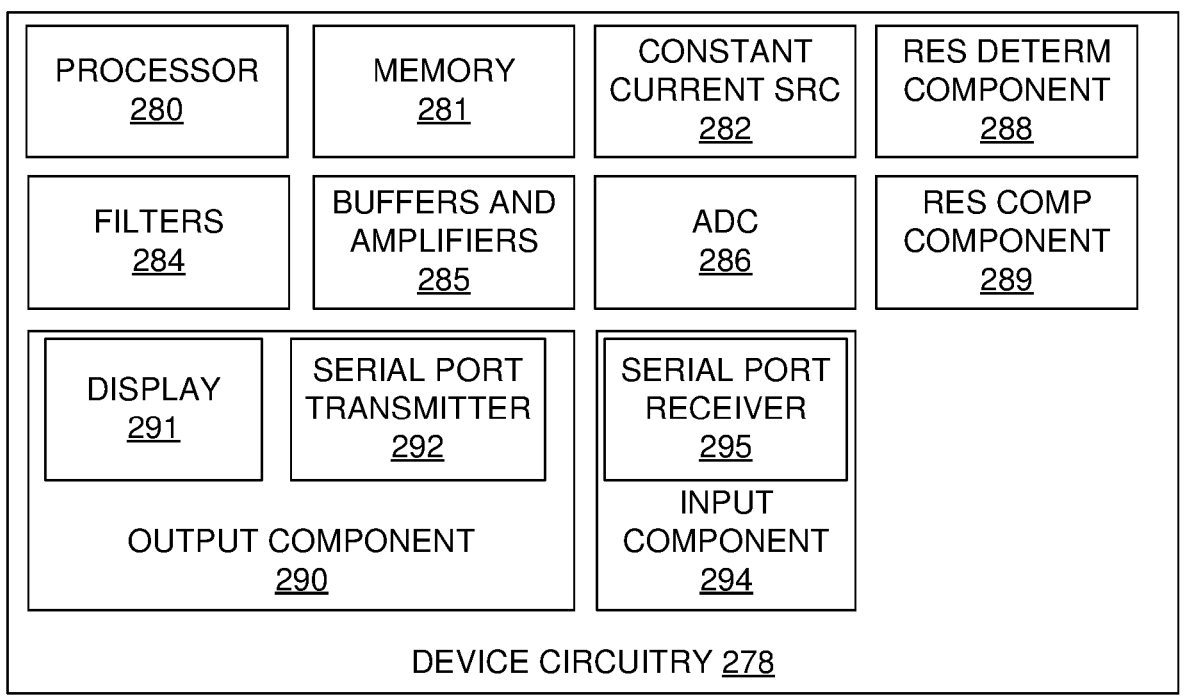
FIG. 6 is a block diagram showing functional blocks of a system according to the invention.

FIG. 6 is a schematic representation showing the functional blocks of the device (210) including its circuitry (278). The circuitry (278) includes a processor (280) on which software may be executed to implement the methods in accordance with this disclosure. The software executed on the processor (280) may implement functional components of the device (210) and its circuitry (278). The software may be stored on a memory (281) and instructions may be provided to the processor (280) to carry out the functionality of the software. Some or all of the software components may be provided by a software application downloadable onto and executable on a point-of-care device, such as a hand held device.

The circuitry (278) of the device (210) further includes a constant current source (282) for injecting an electric current of known, constant, value into a substrate (110) (in use) via the electrodes (230, 232). The constant current source (282) in the present embodiment is a direct current (DC) current source and may have a configurable current output value. The injected current from the constant current source (282) will cause a voltage drop across the substrate (110) in proportion to its resistance. The circuitry (278) may include low pass filters (284) to suppress high frequency noise, thereby to improve the accuracy of measurement of the afore-mentioned voltage. In the present embodiment the low pass filters (284) are RC-filters. The circuitry may further include an amplification stage with voltage buffers and amplifiers (285) to amplify the voltage across the substrate (110) to assist in its measurement.

The amplification stage may be followed by an analogue to digital converter (ADC) (286) for converting the voltage across the substrate (110) to a digital value. The processor (280) may read the converted digital voltage value from the ADC (286) and use this digital representation of the voltage to derive the resistance of the substrate (110). The processor may be configured with the value of the constant current source (282) output and the amplification factor of the amplifiers (285) and may use Ohm's law to programmatically calculate the resistance measurement value with a resistance determining component (288). The ADC (286) may have as many channels as there are receiving zones (270) and electrode pairs to enable individual measurement of the resistance of the substrate (110) in each receiving zone.

The circuitry (278) of the device (210) further includes a resistance comparing component (289) arranged to compare each resistance measurement to the other resistance measurements and assigning an autophagic flux value to the sample. The resistance measurements of each sample may change over time as the proteins (130) in the biological sample bind to the capture agents (120) on the substrate (110). The resistance comparing component (289) may therefore be configured to perform the resistance comparisons at certain time intervals or after a configured time period from the start of the analysis.

The circuitry (278) further includes an output component (290) configured to output a result. The result may include the measured resistance values of the samples and the autophagic flux value assigned to each sample. The output component (290) may include a display (291) to provide a visual output of the results to an operator. The results shown to the operator may include the resistance for each substrate, the amount of each protein detected, and the relative resistance level for the substrates or the assigned level of autophagic flux. The output component (290) may further include a serial port transmitter (292) to transmit data representing the results to an external computer (150) via a serial cable for data logging, further computation, and display. Although the data obtained and calculated during the sample analysis may be sent to an external computer (150) the data may also be stored on the memory (281) of the device (210), at least temporarily.

The circuitry (278) further includes an input component (294) for inputting commands and configuration settings to the device (210). The input component (294) may include a serial port receiver (295) for receiving commands and configuration settings from an external computer (150) via a serial cable.

By comparing the measured (or calculated) resistance for each substrate to the measured the resistance measured for the other substrates, and assigning a level of autophagic flux based on the relative resistance level, to the device (210) may determine the level of autophagic flux in the sample. This comparison may include comparing the relative resistance level with a predetermined value, which may be based on relative resistance levels of subjects with a known autophagic flux level.

Figure 7:
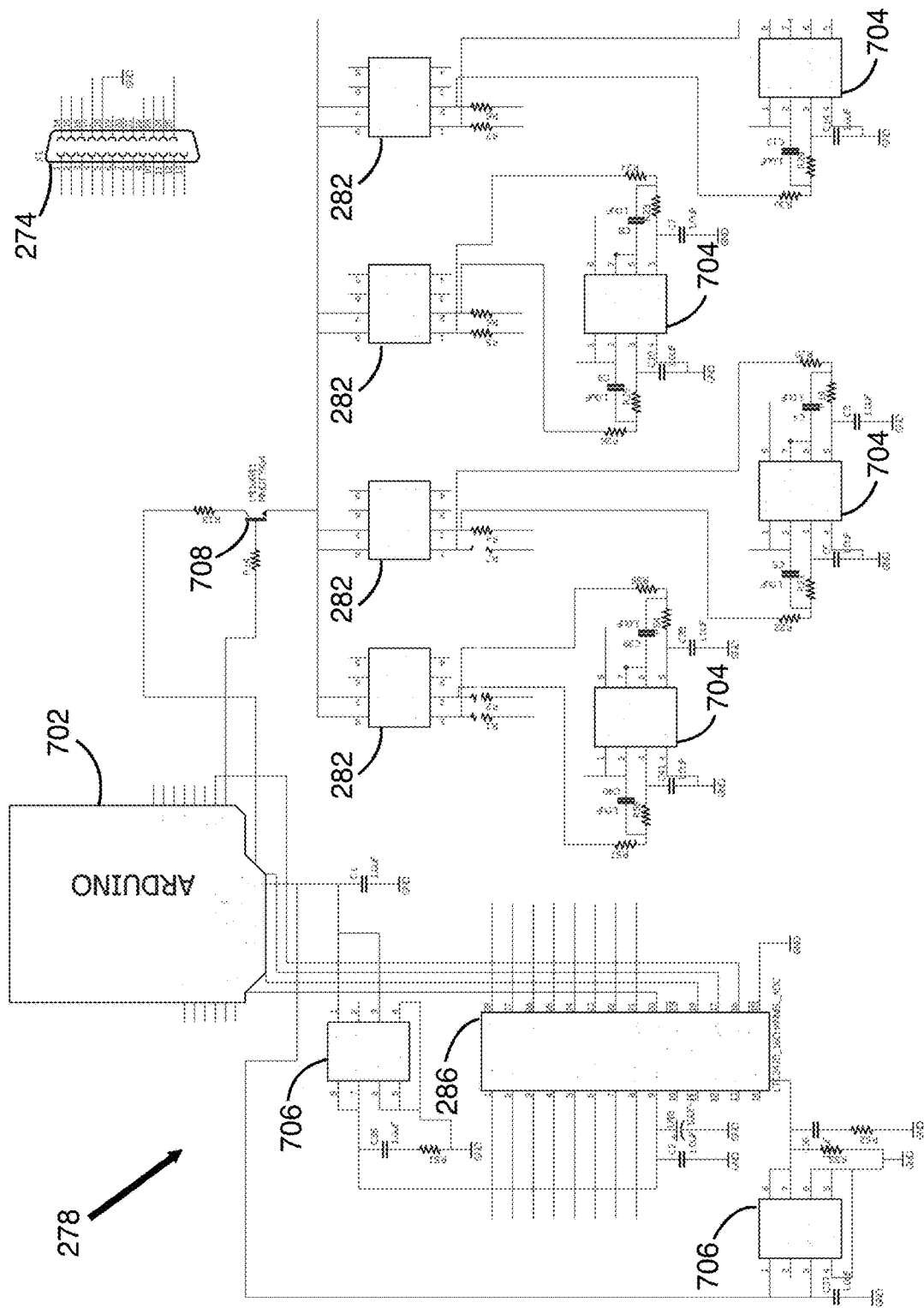
FIG. 7 is an example of a circuit design for performing the method of the invention.

FIG. 7 is a schematic representation of the device circuitry (278) on a component level. It shows, for example, a microprocessor (702) which in the present embodiment is provided by an Arduino™ single-board controller. It will be appreciated by those skilled in the art that the microprocessor (702) may provide a number of the functional blocks of the circuitry (278) shown in FIG. 6, including the processor (280), memory (281), serial port transmitter and receiver (292, 295), resistance determining component (288) and resistance comparing component (289). FIG. 7 further shows the ADC (286) which, in the present embodiment, is an LTC2418 16-channel ADC from Analog Devices™. FIG. 7 also shows an example of a constant current source (282); and a number of operational amplifiers (op-amps) (704).

Various op-amp configurations may be utilised to implement filters (284) as well as buffers and amplifiers (285). FIG. 7 further shows a schematic symbol of the female DB25 connector (274) of the PCB (276) on which the circuitry (278) is provided. Various miscellaneous components are also shown, such as voltage regulators (706) which provide supply voltages or reference voltages, as the case may be. A transistor (708) is provided that enables the microcontroller (702) and its functional blocks to enable and disable the constant current sources (282) as may be required.

Computer-readable media in the form of the various memory components may provide storage of computer-executable instructions, data structures, program modules, software units and other data. A computer program product may be provided by a computer-readable medium having stored computer-readable program code executable by a central processor. A computer program product may be provided by a non-transient computer-readable medium, or may be provided via a signal or other transient means via the communications interface.

Interconnection via the communication infrastructure allows the one or more processors to communicate with each subsystem or component and to control the execution of instructions from the memory components, as well as the exchange of information between subsystems or components. Peripherals (such as printers, scanners, cameras, or the like) and input/output (I/O) devices (such as a mouse, touchpad, keyboard, microphone, touch-sensitive display, input buttons, speakers and the like) may couple to or be integrally formed with the device either directly or via an I/O controller.

The device can be a point-of-care device, such as a device which can be connected to a personal computer, laptop, or handheld device.

The substrate and biological sample can be as described above.

The invention extends even further to a computer-implemented method for determining autophagic flux in a subject. As illustrated in FIG. 9, the computer-implemented method (900) can include: receiving (902) resistance readings from detectors which measure resistances of a plurality of substrates, each of which is configured to bind a protein of interest in a sample. The received resistance readings correspond to individual proteins and their associated relative abundance of flux signature proteins. This resistance reading signal may be an analogue signal and may be converted (904) to a digital signal for further processing by a digital processor and recording (906) the digital resistance signal. The resistance signal of the candidate proteins is processed (908), thereby quantifying the relative changes of the levels of the proteins (based on the resistance readings) as well as the changes relative to a flux-independent protein; and assigning an autophagic flux value to the sample. The assigned autophagic flux value is compared (912) to a predetermined flux range associated with known autophagy dysfunction or associated with ageing, exercise and caloric restriction; and the result is outputted (912) indicating whether the subject from whom the sample was obtained has autophagy dysfunction or is successfully ageing. A readout might be "normal", "detrimental", "abnormal", "enhanced", "diminished", etc.

Figure 10:
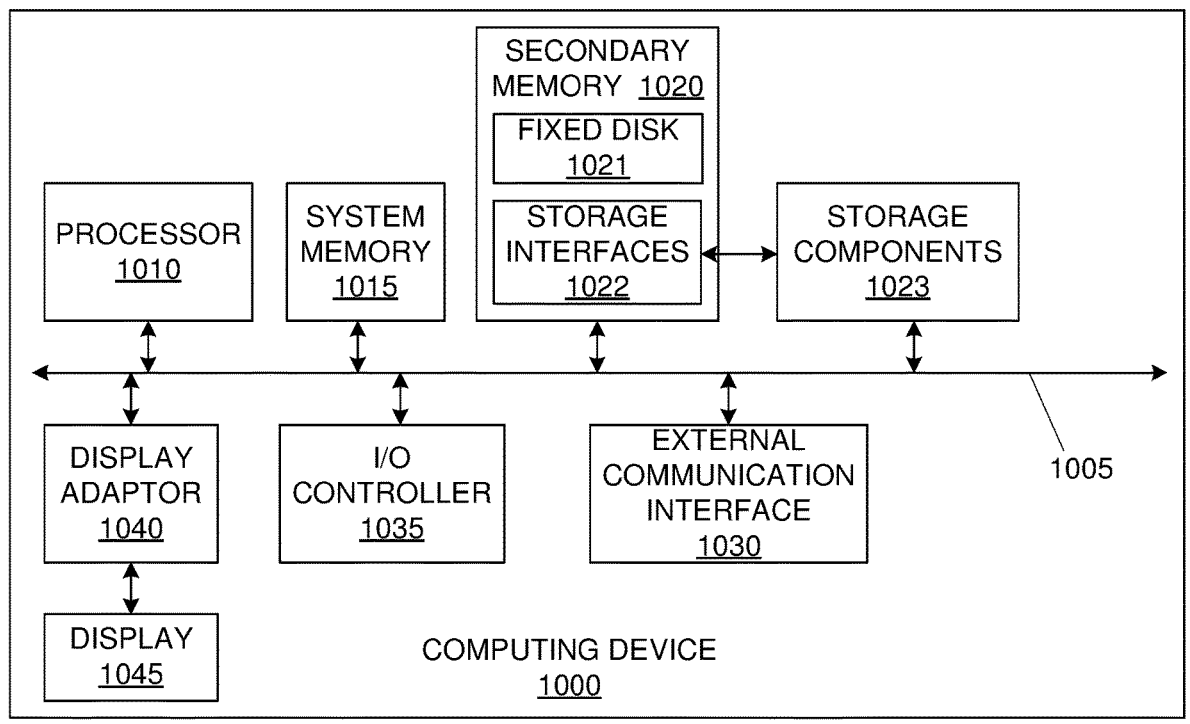
FIG. 10 illustrates an example of a computing device in which various aspects of the disclosure may be implemented.

FIG. 10 illustrates an example of a computing device (1000) in which various aspects of the disclosure may be implemented. The computing device (1000) may be embodied as any form of data processing device including a personal computing device (e.g. laptop or desktop computer), a server computer (which may be self-contained, physically distributed over a number of locations), a client computer, or a communication device, such as a mobile phone (e.g. cellular telephone), satellite phone, tablet computer, personal digital assistant or the like. Different embodiments of the computing device may dictate the inclusion or exclusion of various components or subsystems described below.

The computing device (1000) may be suitable for storing and executing computer program code. The various participants and elements in the previously described system diagrams may use any suitable number of subsystems or components of the computing device (1000) to facilitate the functions described herein. The computing device (1000) may include subsystems or components interconnected via a communication infrastructure (1005) (for example, a communications bus, a network, etc.). The computing device (1000) may include one or more processors (1010) and at least one memory component in the form of computer-readable media. The one or more processors (1010) may include one or more of: CPUs, graphical processing units (GPUs), microprocessors, field programmable gate arrays (FPGAs), application specific integrated circuits (ASICs) and the like. In some configurations, a number of processors may be provided and may be arranged to carry out calculations simultaneously. In some implementations various subsystems or components of the computing device (1000) may be distributed over a number of physical locations (e.g. in a distributed, cluster or cloud-based computing configuration) and appropriate software units may be arranged to manage and/or process data on behalf of remote devices.

The memory components may include system memory (1015), which may include read only memory (ROM) and random access memory (RAM). A basic input/output system (BIOS) may be stored in ROM. System software may be stored in the system memory (1015) including operating system software. The memory components may also include secondary memory (1020). The secondary memory (1020) may include a fixed disk (1021), such as a hard disk drive, and, optionally, one or more storage interfaces (1022) for interfacing with storage components (1023), such as removable storage components (e.g. magnetic tape, optical disk, flash memory drive, external hard drive, removable memory chip, etc.), network attached storage components (e.g. NAS drives), remote storage components (e.g. cloud-based storage) or the like.

The computing device (1000) may include an external communications interface (1030) for operation of the computing device (1000) in a networked environment enabling transfer of data between multiple computing devices (1000) and/or the Internet. Data transferred via the external communications interface (1030) may be in the form of signals, which may be electronic, electromagnetic, optical, radio, or other types of signal. The external communications interface (1030) may enable communication of data between the computing device (1000) and other computing devices including servers and external storage facilities. Web services may be accessible by and/or from the computing device (1000) via the communications interface (1030).

The external communications interface (1030) may be configured for connection to wireless communication channels (e.g., a cellular telephone network, wireless local area network (e.g. using Wi-Fi™), satellite-phone network, Satellite Internet Network, etc.) and may include an associated wireless transfer element, such as an antenna and associated circuitry.

The computer-readable media in the form of the various memory components may provide storage of computer-executable instructions, data structures, program modules, software units and other data. A computer program product may be provided by a computer-readable medium having stored computer-readable program code executable by the central processor (1010). A computer program product may be provided by a non-transient computer-readable medium, or may be provided via a signal or other transient means via the communications interface (1030).

Interconnection via the communication infrastructure (1005) allows the one or more processors (1010) to communicate with each subsystem or component and to control the execution of instructions from the memory components, as well as the exchange of information between subsystems or components. Peripherals (such as printers, scanners, cameras, or the like) and input/output (I/O) devices (such as a mouse, touchpad, keyboard, microphone, touch-sensitive display, input buttons, speakers and the like) may couple to or be integrally formed with the computing device (1000) either directly or via an I/O controller (1035). One or more displays (1045) (which may be touch-sensitive displays) may be coupled to or integrally formed with the computing device (1000) via a display (1045) or video adapter (1040).

The invention also extends to a kit for use in the method. The kit can include a device as described above, capture agents for binding two or more of the proteins mentioned above, two or more substrates as mentioned above (with or without capture agents); and/or instructions and/or software for determining autophagic flux according to the method of the present invention.

The invention will now be described in more detail by way of the following non-limiting examples. In particular, it will be apparent to a person skilled in the art that any combination of flux-dependent proteins can be used to measure the autophagic flux. Also, the calculations provided in examples 1 and 2 should be seen only as one example of how to compare protein levels and changes therein so as to determine autophagic flux. Those skilled in the art will realise that other calculations could be used to compare the respective data sets to determine autophagic flux.

EXAMPLES

Identification of Autophagic Flux-Specific Proteins

Figure 11:
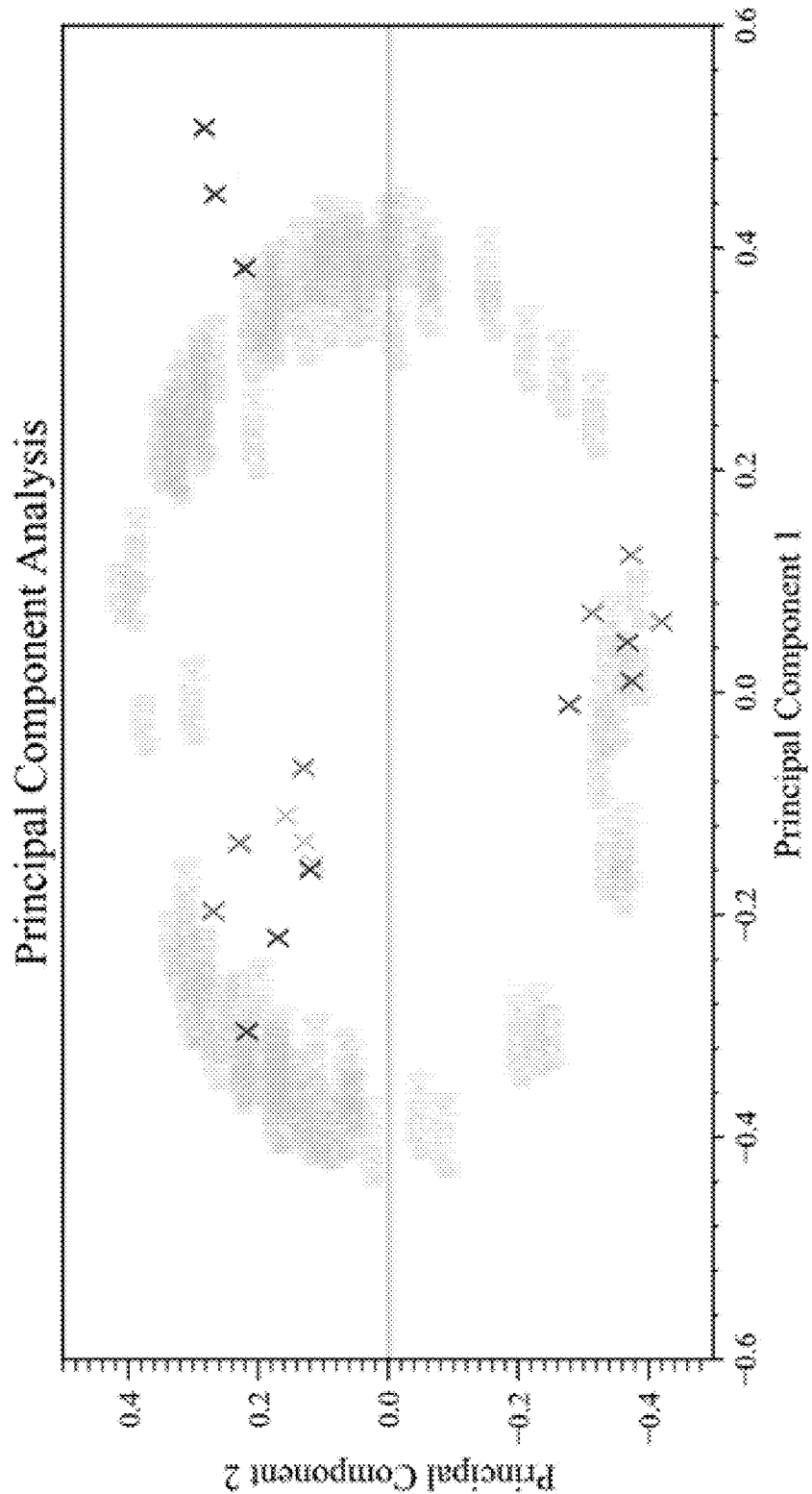
FIG. 11 is a proteome map of known fluxes showing the signature of proteins that change with changing autophagic flux.
Figure 12:
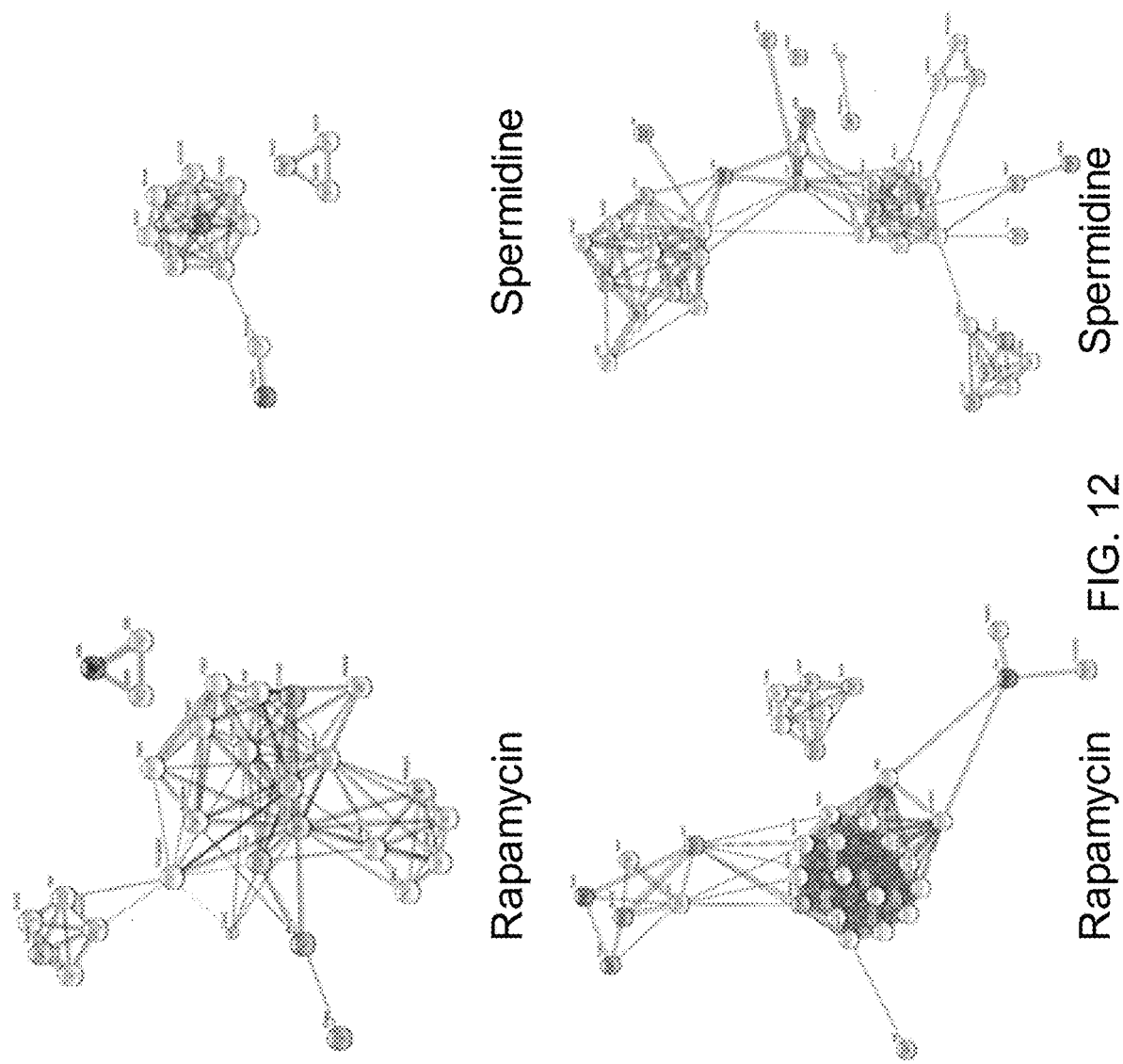
FIG. 12 shows protein clusters that significantly increase (top) and decrease (bottom) with enhanced autophagic flux when two distinct autophagy inducers (rapamycin and spermidine) are used.
Figure 13:
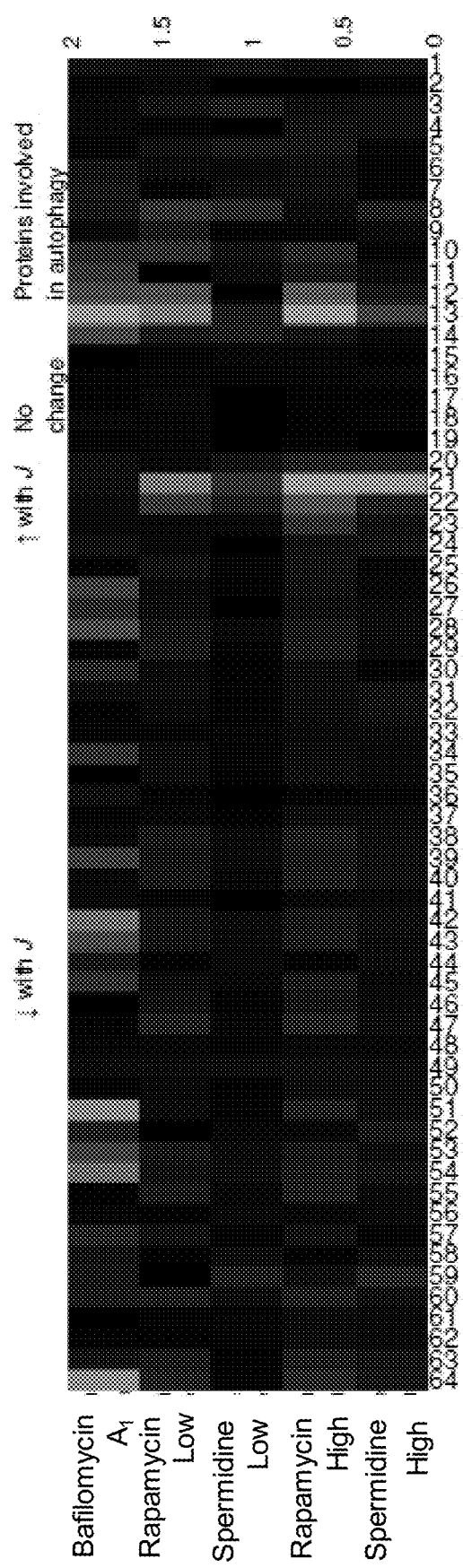
FIG. 13 shows proteins with the most robust flux-related changes, revealing a flux-specific signature.

A previously described method of determining autophagosome flux (PCT/162017/052732, the entire contents of which are incorporated herein) was used to identify proteins that are expressed at different levels with changing autophagic flux (FIG. 13). From a list of 2000 potential proteins, top scoring responding proteins were selected as being suitable for use in the method of the present invention (Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin, Phospho-mammalian target of rapamycin). These include proteins that increase and proteins that decrease with a change in autophagic flux. These proteins, which were well defined in a proteome assessment (FIG. 11), are specifically characterized by either significantly increasing or decreasing in abundance with an incremental increase in autophagic flux. Moreover, the proteins have been selected based on their ability to report on mTOR dependent (rapamycin) or mTOR independent (spermidine) autophagy change (FIG. 12), so as to increase versatility of the sensing device.

LC3 Measurement

A device described above was used to detect levels of LC3 protein (Microtubule associated proteins 1A/1B light chains 3A/LC3A and 3B/LC3B (MAPILC3A/B)). The LC3 and other autophagy-related proteins were prepared using Mouse Embryonic Fibroblast (MEF) cells, cultured in Dulbecco's modified Eagle's medium (DMEM). This was supplemented with fetal bovine serum, Antibiotic-Antimycotic, penicillin, streptomycin and Fungizone antimycotic. The cells were maintained in a humidified atmosphere in the presence of 5% $CO_2$ at 37° C. The MEF cells were subcultured using trypsinisation. The cells were collected in falcon tubes and a 2:1 ratio of DMEM was added. The cells were removed from the containing medium and rinsed with PBS, and then mixed with RIPA buffer in a petri-dish. Lysate samples were collected and sonicated using a Mixsonic (S-4000). The samples were centrifuged at 8000 rpm at 4° C. for 10 min. Thereafter the supernatant was collected and stored at −80° C. for later use.

A lower part of the device was autoclaved to ensure sterility and to remove any remaining reagents from previous tests. This was removed from the autoclave and left in a fume hood to dry. Gold-plated electrodes on an upper part of the device were rinsed with ethanol (70% C2H6O) and left to dry for 10 minutes. 100 μl of PBS-T was added to each receiving zone in the lower part of the device. This ensured consistency between the different receiving zones. A dilution series of the lysate in RIPA buffer was prepared for testing. Typically a 10×, 100× and 1000× dilution of the stock solution was prepared. As negative control, a RIPA solution containing no lysate was prepared.

Rabbit anti-LC3 antibodies (Sigma, #L-8918) were immobilized on the surface of the substrate of the device. The stock concentration of the anti-LC3 antibodies was 2 mg/ml.

Figure 14:
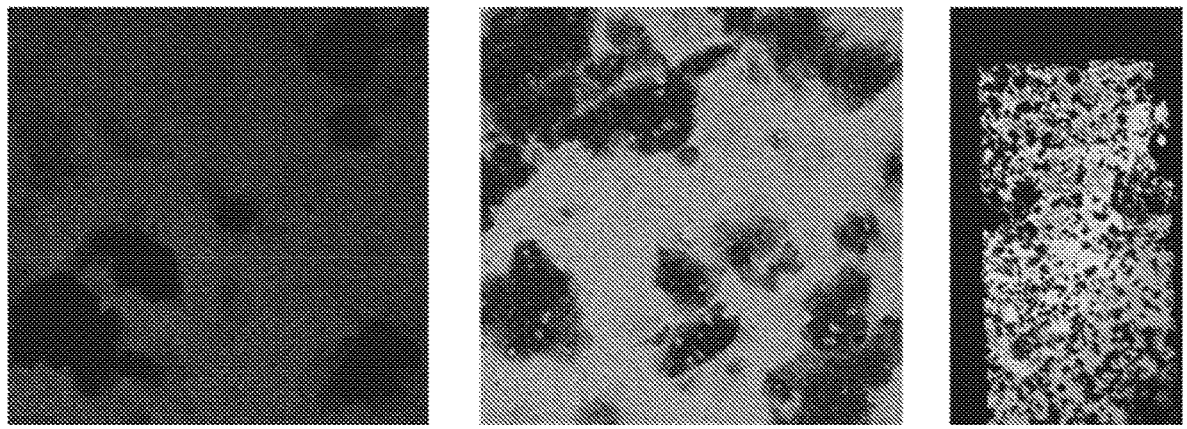
FIG. 14 shows a strong specific fluorescence LC-3 signal (right) compared to a negative control (left). A maximum intensity projection is shown using a LUT (far right).
Figure 15:
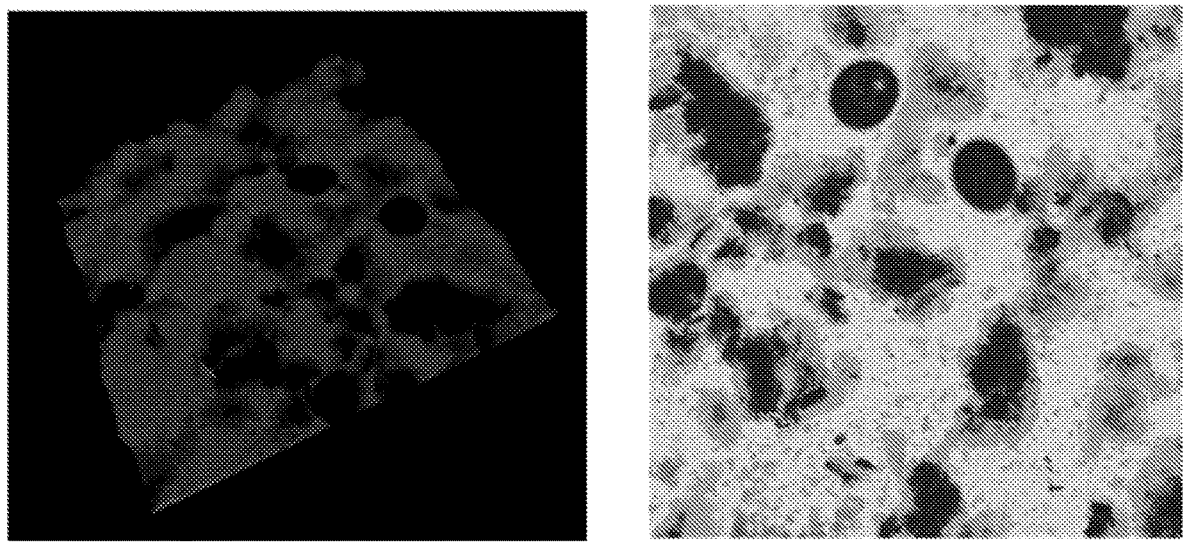
FIG. 15 shows the distribution of positive LC3-based binding, as revealed by 3D rendering of z-stack fiber acquisitions (left) and its maximum intensity projection using a LUT (right).
Figure 16:
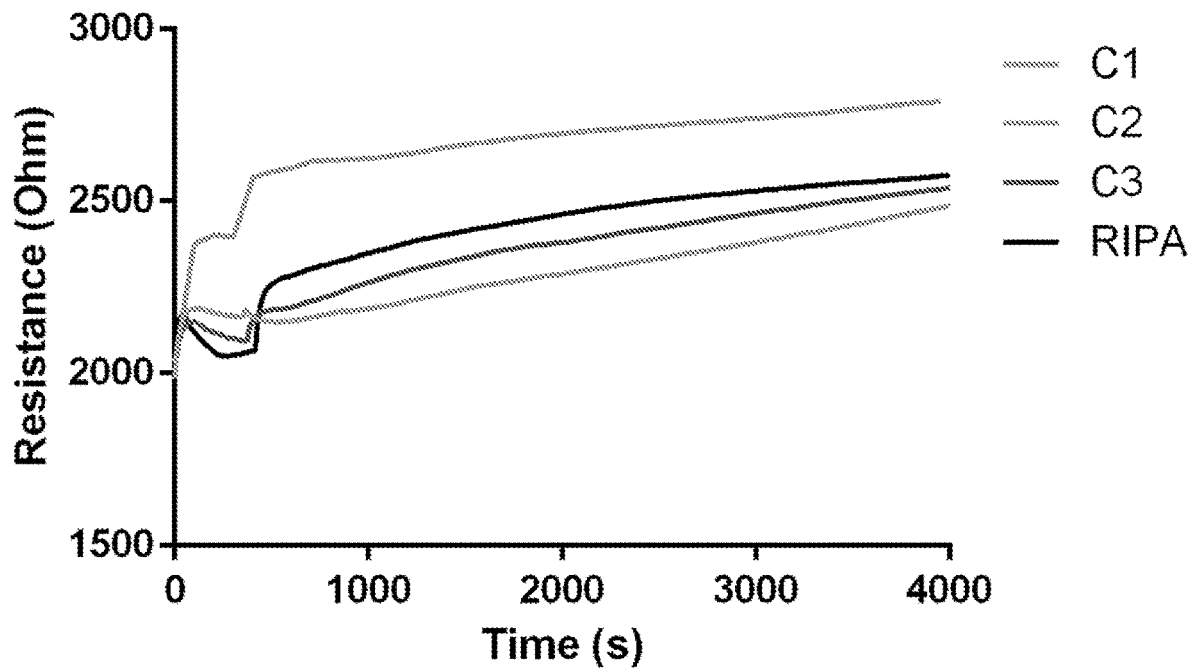
FIG. 16 shows resistance measurements in presence of positive LC3-binding at different concentrations vs a control.
Figure 17:
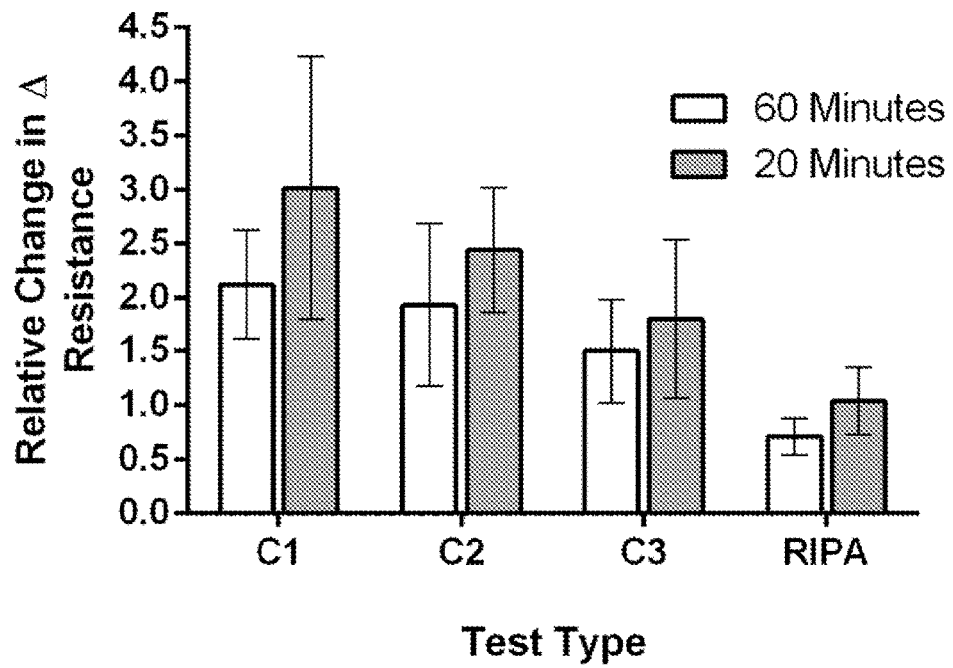
FIG. 17 is a bar graph showing a dose dependent change in resistance after 20 minutes and 60 minutes detecting LC3 protein and a negative control.

Binding experiments confirmed specific binding of LC3 to the antibodies. Little non-specific signal was detected, while the positive sample was characterized by strong fluorescence emission signal (FIGS. 14 and 15). There was a robust increase in resistance in the presence of bound protein-antibody compared to controls (FIG. 16), and it can be seen in FIG. 17 that the change in resistance is dose-dependent. This indicates high sensitivity and specificity for the detection of LC3 protein after both 20 minutes and 60 minutes.

Hypothetical Examples for Determining Autophagic Flux

Example 1:—Comparing Levels of Two Proteins (e.g. Serine/Threonine-Protein Kinase DCLK1 and Histone-Binding Protein RBBP7)

A blood tissue biopsy is obtained from a subject and a protein lysate is prepared by standard protein extraction methods (e.g. Bradford, where, in brief, a protein standard curve is established using bovine serum albumin (BSA) dissolved in RIPA buffer. The protein standards are incubated with the Bradford reagent for five min in the dark and the absorbance values are measured with a universal microplate reader at a wavelength of 595 nm. The absorbance value for 0 μg/μl is subtracted from the absorbance value of the protein standard concentration range. Lysates are incubated with the Bradford reagent for five min in the dark and the absorbance value is determined by subtracting 0 μg/μl from the measured absorbance value of the lysate at 595 nm. The protein concentration of the lysates to be assessed are determined by reading them off the standard curve). Equal portions of the protein lysate are introduced into two wells of a device as described above. A first substrate coated with anti-Serine/threonine-protein kinase DCLK1 antibodies is inserted into the protein lysate in well 1 and a second substrate coated with anti-Histone-binding protein RBBP7 antibodies is inserted into the protein lysate in well 2. The resistance across each substrate is measured before it is inserted into the well, and is again measured after a period of, for example, 20 minutes. The change in resistance in well 1 (due to Serine/threonine-protein kinase DCLK1 from the sample binding to the $1^{st}$ substrate) is, for example 1.2. This protein decreases with autophagy flux. The change in resistance in well 2 (due to Histone-binding protein RBBP7 from the sample binding to the $2^{nd}$ substrate) is, for example, 3.7. This protein increases with autophagy flux. Both proteins are expressed over the abundance of the protein DnaJ homolog subfamily B member 4, a protein which does not change with autophagy flux. This protein abundance is determined in a similar manner. Its change in resistance is, for example, 2.0. Hence, the proteins are now expressed relative to 2.0, i.e. DLCK1: 1.2/2.0=0.6 and RBBP7: 3.7/2.0=1.85. The protein ratio of those which increase with flux are now expressed over the proteins that decrease with flux, i.e. 1.85/0.6=3.08, which is a measure of the autophagy flux in the sample, based on the proteins DCLK1 and RBBP7. In addition, a subtractive value will be provided, subtracting the ratio derived from proteins with decreasing flux from those derived from proteins with increasing flux: 1.85−0.6=1.25. The biopsy sample can now be compared to its control sample (a non-pathological control sample, i.e. healthy tissue from the same subject).

Example 2:—Comparing Levels of 4 Proteins (Sequestosome-1, Acetoacetyl-CoA Synthetase, V-Type Proton ATPase Catalytic Subunit A, and Glyceraldehyde-3-Phosphate Dehydrogenase)

A tissue biopsy can be prepared as for example 1. Equal portions of the protein lysate are introduced into four wells of a device as described above. A first substrate coated with anti-Sequestosome-1 antibodies is inserted into the protein lysate in well 1, a second substrate coated with anti-Acetoacetyl-CoA synthetase antibodies is inserted into the protein lysate in well 2, a third substrate coated with anti-V-type proton ATPase catalytic subunit A antibodies is inserted into the protein lysate in well 3 and a fourth substrate coated with anti-Glyceraldehyde-3-phosphate dehydrogenase antibodies is inserted into the protein lysate in well 4. The resistance across each substrate is measured before the substrate is inserted into the well, and is again measured after a period of 20 minutes.

In a similar manner, the change in resistance is plotted over the change in resistance derived from the flux-resistant control protein protein DnaJ homolog subfamily B member 4, a protein which does not change with autophagy flux. The change in resistance in well 1 is W1, the change in resistance in well 2 is ×1, the change in resistance in well 3 is Y1 and the change in resistance in well 4 is Z1. The relative abundance of proteins increasing with flux will be described in this manner, as well as the relative abundance of proteins decreasing with flux (in this case, Glyceraldehyde-3-phosphate dehydrogenase and Sequestosome-1). Next, the sum of the protein ratio of those increasing with flux are expressed over the sum of proteins that are decreasing with flux, which is a measure of the autophagy flux in the sample, based on the proteins Sequestosome-1, Acetoacetyl-CoA synthetase, V-type proton ATPase catalytic subunit A, and Glyceraldehyde-3-phosphate dehydrogenase. In addition, a subtractive value will be provided, subtracting the ratio derived from proteins with decreasing flux from those derived from proteins with increasing flux. The biopsy sample can now be compared to its control sample (a non-pathological control sample, i.e. healthy tissue from the same subject).

The invention claimed is:

1. A method for determining autophagic flux, the method comprising the steps of:
   determining, in a biological sample from a subject, the level of at least two proteins which are overexpressed or underexpressed with a change in autophagic flux, wherein the proteins are selected from the group consisting of Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin and Phospho-mammalian target of rapamycin;
   determining, in the biological sample, the level of a reference protein which is not differently expressed with a change in autophagy;
   comparing the level of each of the at least two proteins to the level of each of the other proteins which are overexpressed or underexpressed with a change in autophagic flux and comparing these proteins to the level of a reference protein; and
   obtaining a flux value for the sample.

2. A method according to claim 1, wherein the flux value of the sample is compared to a predetermined flux value or range associated with a known autophagy flux in order to determine whether there is autophagy dysfunction in the subject.

3. A method according to claim 2, wherein the autophagy dysfunction is an indicator of a neurodegenerative disease or condition selected from the group consisting of cancer, a heart condition, an immune condition and an aging-related condition.

4. A method according to claim 1, wherein the step of determining the level of the at least two proteins in the sample which are overexpressed or underexpressed with a change in autophagic flux is performed by capturing the proteins onto a substrate and determining the amount of protein that has been captured,
   wherein the amount of protein captured on the substrate is determined by measuring the electrical resistance across the substrate.

5. A method according to claim 4, wherein capture agents are used to capture the proteins onto the substrate, wherein the capture agents are selected from the group consisting of antibodies or antibody fragments, affibodies, ankyrin repeat proteins, armadillo repeat proteins, nucleic acid aptamers, peptides, carbohydrate ligands, synthetic ligands, luminescent conjugated oligothiophene (LCO) markers and synthetic polymers.

6. A device for determining autophagic flux in a sample from a subject, the device comprising:
   a housing;
   a plurality of receiving zones located in the housing, each receiving zone configured for receiving a substrate and a portion of a biological sample from a subject;
   a set of electrodes for each receiving zone, each set of electrodes positioned in the housing so as to extend into a receiving zone and to come into contact with the substrate when the substrate is in the receiving zone;
   wherein each set of electrodes is connectable to circuitry which includes:
      a resistance determining component in communication with the electrodes arranged to determine a resistance of the relevant substrate when in contact with the electrodes, wherein the resistance measurement for each substrate corresponds to the level of protein bound to the substrate;
      a processor configured to compare the resistance measurement of each substrate to the resistance measurements of the other substrates and assign an autophagic flux value to the biological sample according to the method of claim 1.

7. A device according to claim 6, which includes the substrate in each receiving zone, wherein the substrate is a carbon substrate in the form of nanofibres or nanowires.

8. A device according to claim 6, wherein the substrate in each receiving zone is coated with capture agents for binding proteins from the sample, the protein being a protein which is overexpressed or underexpressed with a change in autophagic flux and which is selected from the group consisting of Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin and Phospho-mammalian target of rapamycin or being a protein which is not differently expressed with a change in autophagy;
   wherein each substrate binds a different protein selected from the group above and at least one substrate binds the protein which is not differently expressed with a change in autophagy.

9. A device according to claim 6, wherein the housing comprises separable upper and lower parts, the receiving zones being located in the lower part of the housing and the upper part of the housing being configured to attach onto the lower part so that each receiving zone is covered and so that the electrodes come into contact with the substrate when the substrate is in the receiving zones.

10. A device according to claim 6, wherein the autophagic flux value assigned by the processor indicates the autophagic flux of the sample or whether or not the subject has autophagy dysfunction.

11. A computer implemented method for diagnosing autophagy dysfunction in a subject, the computer performing steps comprising:
   receiving inputted subject data comprising values corresponding to levels of two or more proteins in a biological sample from the subject, wherein the proteins are selected from the group consisting of Serine/threonine-protein kinase DCLK1, Serine-tRNA ligase cytoplasmic (SARS), Sequestosome-1, Acetoacetyl-CoA synthetase, V-type proton ATPase catalytic subunit A, Glyceraldehyde-3-phosphate dehydrogenase, Histone-binding protein RBBP7, DnaJ homolog subfamily B member 4, Microtubule-associated proteins 1A/1B light chain 3B, Cysteine protease ATG4B, Lysosome-associated membrane glycoprotein 2, Tubulin beta-2A chain, Mammalian target of rapamycin and Phospho-mammalian target of rapamycin;

comparing the value of each protein to the values for the other proteins and to the value for a reference protein which is not differently expressed with a change in autophagy;

assigning a flux value for the sample based on the relative values or levels of the proteins in the sample; and displaying information regarding whether the subject has autophagy dysfunction or not.

12. A computer implemented method according to claim 11, wherein the inputted subject data comprises resistance readings corresponding to the amount of the proteins in the biological sample.

* * * * *